United States Patent [19]

Watson et al.

[11] Patent Number: 5,082,489
[45] Date of Patent: Jan. 21, 1992

[54] COMPOSITION FOR BIOCONTROL OF WILD BUCKWHEAT

[75] Inventors: Alan K. Watson, Pincourt; Lee A. Wymore, Ste-Anne-de-Bellevue, both of Canada

[73] Assignee: The Royal Institution for the Advancement of Learning (McGill University), Montreal, Canada

[21] Appl. No.: 475,954

[22] Filed: Feb. 6, 1990

[51] Int. Cl.$^5$ .............................................. A01N 37/10
[52] U.S. Cl. .......................................... 71/79; 71/115; 71/116
[58] Field of Search ............................ 71/79, 116, 115

[56] References Cited

U.S. PATENT DOCUMENTS 4,496,390 1/1985 Hatton et al. .............................. 71/92
4,776,873 10/1988 Caulder et al. .......................... 71/79

OTHER PUBLICATIONS

*Weeds*—Quimby, Effect of Dicamba on Wheat and Wild Buckwheat . . . , vol. 14:229–232.

*Primary Examiner*—Marianne Cintins
*Assistant Examiner*—Jessica Nguyen
*Attorney, Agent, or Firm*—Cushman, Darby & Cushman

[57] ABSTRACT

The present invention is concerned with a novel bioherbicide and its use alone or in compositions, to control the growth of *Polygonum convolvulus* in agricultural crops such as cereals and other cultivated crops. The present invention is also concerned with a synergistic composition of the novel bioherbicide and a chemical herbicide. Specifically, the new fungus is Phoma sp. ATCC 20982.

7 Claims, No Drawings

COMPOSITION FOR BIOCONTROL OF WILD BUCKWHEAT

BACKGROUND OF THE INVENTION

Wild buckwheat (*Polygonum convolvulus* L.) is an annual taprooted weed. It occurs in agricultural areas in all of the Canadian provinces but is reported to be more abundant in the west than in the east. It is native to Europe and was first collected in Canada in Manitoba in 1873.

Wild buckwheat overwinters as achenes. It has a climbing growth habit which allows it to compete well in stands of cereals and other tall crops. This growth habit allows for rapid spread and coverage of bare ground or open spaces. The number of achenes produced by a single plant varies with soil type and seeding date, but under noncompetitive conditions a single plant can produce up to 30,000 achenes. Seed dispersal is normally accomplished by disturbance by farm machinery and long distance dispersal may take place through contaminated crop seed.

Due to its growth habit and abundant seed production, wild buckwheat is a competitive weed that causes significant losses in grain crops. Herbicides registered for use on wild buckwheat include dicamba, bromoxynil, combinations of these chemicals with 2,4-D or MCPA and other herbicides alone, as formulated mixtures, or in various combinations.

However, the efficiency of these chemicals is sometimes limited. Furthermore, the excessive use of chemicals is of concern for the environment and human health. It would therefore be highly desirable to have an herbicidal composition which has better and more selective properties against wild buckwheat, and which reduces the input of chemicals into the environment.

SUMMARY OF THE INVENTION:

The present invention relates to a novel bioherbicide which is effective in controlling the growth of *Polygonum convolvulus* (wild buckwheat) when used in accordance with the process described herein.

More specifically, the present invention relates to the use of composition of the fungus Phoma sp. in association with an agricultural carrier to control buckwheat infestation in agricultural crops.

Also in accordance with the present invention, there is provided a synergistic composition comprising the fungus Phoma sp., a chemical herbicide and an agricultural carrier to control buckwheat infestation.

DETAILED DESCRIPTION OF THE INVENTION

The fungal pathogen of the present invention causes a destructive leaf blight on wild buckwheat plants growing in field plots. Diseased leaves were collected and following a commonly used method, pieces of leaf tissue were cut from the margins of lesions and immersed in 10% (v/v) Javex (0.6% NaClO) for 3 min. Surface-disinfested tissue was drained on paper towels and small (1 mm dia.) pieces of tissue were aseptically cut and placed on acidified potato dextrose agar (APDA) in petri dishes. After 2 days, hyphae growing from leaf tissue were transferred to fresh APDA.

Additional isolations were made from leaves collected and air-dried for 4 months. Three single-spore isolates (A1, B2, A3) from dried leaves were identical to those obtained from fresh tissue and were selected for further study. Stock cultures were maintained on agar slants under oil at 3° C. in a refrigerator. One such isolate was identified as Phoma sp.

Numerous plant pathogens being evaluated for use as bioherbicides appear to be only partly effective when applied alone. In combination with chemical herbicides, however, they may be more effective. If used in combination with a chemical herbicide, such bioherbicides may allow a reduction in chemical use and help alleviate safety and environmental concerns.

Phoma sp. is such a plant pathogen. It causes a severe foliage blight on wild buckwheat. It produces numerous necrotic lesions on inoculated leaves and some lesions expand rapidly and kill leaves. It causes mortality of plants, however, only when applied at high inoculum densities to plants at the cotyledon stage or when environmental conditions are highly favorable with warm temperatures and long moist periods. In combination with the chemical herbicides dicamba or MCPA it causes more mortality of wild buckwheat.

A subculture of Phoma sp. has been deposited in the permanent collection of the American Type Culture Collection, Rockville, Md., U.S.A., on Feb. 5, 1990 under the Budapest treaty. The culture was assigned the accession number ATCC 20982 by the repository. The deposit is available to the public upon the grant of a patent disclosing it. However, it should be understood that the availability of a deposit does not constitute a license to practice the subject invention in derogation of patent rights granted by governmental action.

In accordance with a further aspect of the present invention, it has been found that the fungal pathogen Phoma sp., when combined with a chemical herbicide, leads to a synergistic composition which possesses remarkable properties against wild buckwheat. The preferred chemical herbicides of the present invention are dicamba and MCPA. These chemical herbicides were known to possess some herbicidal properties against buckwheat. However, when they are combined with the fungus Phoma sp. of the present invention, the synergistic effect resulting from this combination gives a much more effective composition to fight wild buckwheat. Herbicides which have general broadleaf activity and which have may also act synergistically with the fungus Phoma of the present invention further include clopyralid, DPX M6316, chlorsulfuron, fluroxypyr, pyridate, or formulated mixtures such as dicamba/2,4-D/mecoprop, dicamba/MCPA/mecoprop, diacmba/MCPA, diclorprop/2,4-D, bromoxynil/MCPA, or tank mix of two or more of the herbicides listed above, including dicamba and MCPA.

The actual recommended rate of application for MCPA alone against wild buckwheat, is about 1.2 kg/hectare. Furthermore, when the chemical herbicide is dicamba, the recommended rate is 0.3 to 0.6 kg/hectare. However, when used in combination with the fungus Phoma sp. of the present invention, the rate of application is reduced to 0.4 to 0.8 kg/hectare and 0.1 to 0.3 kg/hectare for MCPA and dicamba respectively.

The concentration of the fungus Phoma sp. in the composition of the present invention, is from about $10^3$ tp $10^7$ spores/ml of carrier. Also, the application rate of the composition is from about $10^5$ to $10^9$ spores/m$^2$.

The present invention will be further illustrated by the following Examples, which are representative, and do not restrict the scope of the invention in any way.

EXAMPLE I

This example illustrates the production of wild buckwheat plants, production of fungal inoculum for application to the plants, and disease development on the plants.

Wild buckwheat seeds were obtained from Valley Seed Service, Fresno, Calif. Seeds were immersed in 95% sulfuric acid ($H_2SO_4$) for 15 min, rinsed under running tap water, and placed on moistened filter papers in glass petri dishes. Dishes with seeds were incubated at 3° C. for 48 hr followed by incubation at 30° C. for 48 hr. Germinated seeds were then planted in 10 cm pots in potting medium (Pro-Mix BX, Premier Brands, Inc., Stamford, Conn.) and grown in growth chambers (14 hr photoperiod, 400 uEm$^{-2}$s$^{-1}$, 24°/18° C. day/night temperature). Seeds were planted four per pot and seedlings were thinned to three per pot prior to treatment.

One liquid culture medium (V-8 medium) and eight solid agar media were evaluated for sporulation by isolates A1, B2, and A3 and for possible use as growth media for inoculum production for experiments: 1) Difco potato dextrose agar (PDA) prepared according to package instructions, 2) half-strength PDA (½PDA, 19.5 g Difco PDA, 10 g Bacto agar, 1000 ml $H_2O$), 3) ½PDA with half-strength torula yeast agar (7.5 g torula yeast, 0.5 g $KH_2PO_4$, 0.25 g $MgSO_4.7H_2O$, 19.5 g Difco PDA, 10 g Bacto agar, 1000 ml $H_2O$), 4) ½PDA with plant extract (19.5 g Difco PDA, 10 g agar, *Polygonum convolvulus* extract [prepared by boiling 200 g chopped wild buckwheat leaves and stems in 1000 ml deionized $H_2O$, straining through cheesecloth, and autoclaving for 20 min on consecutive days] added to the medium at 5, 10, or 20% [v/v], $H_2O$ to make 1000 ml), 5) V-8 juice agar (200 ml V-8 juice, 20 g Bacto agar, 800 ml $H_2O$, adjusted to pH 6 with NaOH), 6) cornmeal agar (CMA), (7) CMA with 10% plant extract (prepared as above), and 8) CZ-8. The media were streaked with spore suspensions obtained from cultures grown on ½PDA with 10% plant extract or agar plugs with mycelium from cultures grown on PDA were inverted and placed in the center of each dish. Cultures were sealed with parafilm and incubated at 24° C. in the dark or at room temperature under near ultraviolet light (NUV). After 1-3 wk, cultures were visually compared for production of pycnidia and exuded droplets of conidial matrix with spores.

Inoculum was also produced on detached leaves of wild buckwheat. Leaves cut from plants grown in growth chambers were placed on moist filter papers in petri dishes (2.5 ml deionized $H_2O$ and 2-3 leaves/plate) and autoclaved for 20 min on consecutive days. Agar plugs (6 mm dia.) with mycelium cut from the margin of colonies growing on PDA were inverted and transferred to the center of each dish containing leaves. Leaf cultures were incubated and evaluated as described above.

Spores were collected from agar plates and leaf cultures by flooding them with deionized water and scraping the surface of the colonies with a sterile wire loop or spatula. Resulting suspensions were filtered through 8 layers of cheesecloth and washed by centrifugation at 7000 RPM for 10 min. The supernatant was discarded and the spore pellet was resuspended in deionized water. The inoculum density was adjusted to the desired level with deionized water and spores were applied to plants at a rate of 500 l of water/ha in a spray chamber using a Teejet full cone nozzle (TG 0.7).

Conidia of each of the three isolates grown on ½PDA with 10% plant extract were used to inoculate wild buckwheat seedlings grown in growth chambers. The plants were at the 3-leaf stage (approximately 21 days after planting germinated seeds) when inoculated with Phoma sp. at an inoculum density of approximately $5 \times 10^7$ spores/m$^2$ (approximately 10$^6$ spores/ml applied at 500 l/ha). Control plants were sprayed with deionized water. Immediately after treatment all plants were placed in a dark dew chamber with an air temperature of 24° C. After 24 hr the plants were returned to the growth chamber. Disease development was observed after 14 days and isolations were made from lesions.

Isolates A1, B2, and A3 were identified as Phoma sp. based on the production of ostiolate pycnidia and hyaline, single-celled conidia.

Phoma sp. failed to sporulate in liquid culture. On solid agar media, all three isolates produced pycnidia most abundantly on ½ PDA with 10% plant extract, ½ PDA with half-strength torula yeast agar, and PDA. There was relatively little pycnidium production on any of the other media. Pycnidium production was increased when plates were incubated under NUV. More pycnidia were produced when spore suspensions were streaked on plates than when agar plugs with mycelium were used. Inoculum production on solid agar media, however, was generally insufficient for use in inoculation experiments.

Although variable, pycnidium production on autoclaved wild buckwheat leaves was more abundant than on solid agar media. Sufficient inoculum was produced by 20-30 leaf cultures for most laboratory and greenhouse inoculation experiments.

Two weeks after treatment, all inoculated plants had developed symptoms similar to those observed in the field. Two types of leaf lesions were observed. Small lesions (approximately 1-2 mm dia.) with tan or white necrotic centers surrounded by a red border were produced most commonly. Larger lesions (approximately 1-2 cm dia.) were also produced. The large lesions were tan or light brown and appeared to originate from small lesions. The large lesions expanded rapidly and resulted in the death and abscission of infected leaves. Pycnidia were often produced on the dead leaves. Isolations from both types of lesions yielded organisms identical to the original isolates.

EXAMPLE II

This example illustrates the effect of temperature on conidium germination and growth of mycelium, important biological characteristics of the fungus.

Conidia of isolate A1 were collected from leaf plates as described above. Some conidia were used after one centrifugation and others were washed two additional times by centrifugation and resuspension in deionized water (pH=4.0). Inoculum density was adjusted to $2 \times 10^5$ spores/ml. Two 30 µl droplets of each spore suspension were placed on clean glass slides supported on bent glass rods in petri dishes with filter papers moistened with a 10% (v/v) glycerine solution. The petri dishes were sealed with parafilm and incubated for 18 hr at 18, 24, and 30° C. Spore germination was determined by observing the droplets with the aid of a compound microscope (100×) and counting 100 spores in 5 random fields per drop for a total of 1000 spores per treatment. Spores were recorded as germinated if a germ tube had been produced which was as long as the diameter of the spore. The experiment was repeated once.

There was no significant effect of washing on spore germination and the highest level of germination occurred at 30° C. (Table 1). Germination was significantly less at cooler temperatures.

TABLE 1

Spore germination (%) of Phoma sp. isolate A1 following one or three washings by centrifugation and incubation for 18 hr at different temperatures.

| Temperature (°C.) | Washed by centrifugation: 1× | 3× | Row mean[a] |
|---|---|---|---|
| 18 | 31[a] | 30[a] | 31[b] |
| 24 | 64 | 69 | 66 |
| 30 | 75 | 77 | 76 |

[a]Data in these two columns are pooled treatment means for two replications of the experiment.
[b]Data in this column are pooled means for temperature averaged over one and three washings and for two replications of the experiment. Factorial analysis of variance indicated no significant effect of washing or interaction and LSD = 3 for mean percent germination at the three temperatures ($\alpha$ = 0.05).

Agar plugs (6 mm diameter) with mycelium cut from the margins of actively growing PDA cultures of the three Phoma isolates were inverted and placed separately on the centers of PDA plates. Plates were incubated at 15, 18, 21, 24, 27, and 30° C. for 7 days. Colony diameters were recorded daily by measuring two diameters at right angles to each other. There were four plates per isolate per temperature and the experiment was repeated once.

After three days of growth, the maximum colony diameter for all three isolates was obtained at 24° C. and there was no significant difference between 24° and 27° C. (Table 2). At all incubation temperatures except 30° C., all three isolates had grown to cover the surface of the PDA plates after 6-7 days of incubation. At 30° C., however, the growth curves had leveled off and the fungus did not cover the surface of the agar by the completion of the experiment.

TABLE 2

Effect of temperature on mycelial growth of three Phoma sp. isolates on PDA in petri dishes[a,b].

| Incubation temperature (°C.) | Isolate A1 | B2 | A3 |
|---|---|---|---|
| 15 | 42cd | 39cd | 39c |
| 18 | 47c | 42c | 44c |
| 21 | 64b | 59b | 57b |
| 24 | 73a | 71a | 68a |
| 27 | 71a | 71a | 69a |
| 30 | 37d | 36d | 38c |

[a]Data are mean colony diameters (mm) for two pooled experiments with four replicate petri dishes for each experiment. Data were collected after three days of incubation.
[b]Values in a column followed by the same letter are not significantly different according to the Waller-Duncan K-ratio t test ($\alpha$ = 0.05).

EXAMPLE III

This example illustrates the effects of dew period temperature and duration on disease development and biomass of wild buckwheat plants inoculated with Phoma sp. isolate A1.

Wild buckwheat seedlings at the 2-leaf stage (15 days after planting germinated seeds) were inoculated with Phoma sp. isolate A1 at an inoculum density of $1 \times 10^9$ conidia/m$^2$. Inoculated plants were placed in dew chambers calibrated to provide air temperatures of 15°, 21°, or 27° C. Moisture conditions in the dew chambers were monitored using a leaf wetness digital recorder (model DP223 with leaf leaf wetness seensor LWS 223, Omnidata Int., Inc., Logan, Utah). After 6, 12, 18, 24, and 30 hr some pots were removed and transferred to the growth chamber. There were uninoculated controls included at all temperature/duration combinations. Additional controls were placed immediately in the growth chamber without receiving a dew period. Disease severity was rated on leaf two after 2 wk using the Barratt-Horsfall scale and by counting numbers of lesions. Disease ratings were converted to midpoint percentages prior to analysis. After 4 wk, mortality was recorded and plants were harvested by cutting the stems at the height of the cotyledonary node. Plants were placed in paper bags, dried at 60° C. for 7 days, and weighed. There were three pots per treatment with three plants per pot and the experiment was repeated once using a lower inoculum density (9.4 $\times 10^7$ conidia/m$^2$). The experiment was also repeated using dew period air temperatures of 18°, 24°, and 30° C.

Discussion and conclusions for this and subsequent sections are based on regression analyses of the data. Data are presented, however, in tabular format and significant differences are presented as indicated by the Waller-Duncan K-ratio t test. The percentage of infected leaves increased with increasing dew period duration and with increasing dew period temperature (Table 3). No infection occurred on inoculated plants which did not receive a dew period. Disease severity as measured by Barratt-Horsfall ratings and by numbers of lesions per leaf also increased with increasing dew duration and with increasing temperature (Table 3). The maximum disease severity occurred following a 30 hr moist period at 27° C. The biomass of inoculated plants expressed as a proportion of the biomass of uninoculated plants which received the same dew period duration and temperature treatments also decreased with increasing dew period duration and temperature (Table 3). Little mortality occurred following any of the treatment combinations. Three of nine plants (33%) were killed following the 30 hr dew period at 27° C. and one of nine plants (11%) was killed following the 12 hr dew period at 27° C.

TABLE 3

Effect of dew period temperature and duration on disease development and biomass of plants inoculated with Phoma sp. isolate A1[a].

| Dew Period Temperature (°C.) | Duration (hr) | Infected leaves (%)[b] | Tissue covered with lesions (%)[c] | Lesions/ leaf[d] | Biomass (proportion of control)[e] |
|---|---|---|---|---|---|
| 15 | 6  | 0 e    | 0 c  | 0.0 c  | 0.876 bcd |
| 15 | 12 | 0 e    | 0 c  | 0.0 c  | 0.882 bcd |
| 15 | 18 | 11 de  | 0 c  | 0.4 bc | 0.914 bcd |
| 15 | 24 | 67 abc | 2 c  | 1.4 bc | 1.171 a |
| 15 | 30 | 56 abcd| 1 c  | 1.2 bc | 0.747 de |
| 21 | 6  | 0 e    | 0 c  | 0.0 c  | 1.077 ab |
| 21 | 12 | 22 cde | 1 c  | 0.7 bc | 0.869 bcd |
| 21 | 18 | 22 cde | 1 c  | 0.4 bc | 0.708 de |
| 21 | 24 | 22 cde | 1 c  | 0.3 bc | 0.879 bcd |
| 21 | 30 | 78 ab  | 27 b | 3.4 ab | 0.816 cd |
| 27 | 6  | 0 e    | 0 c  | 0.0 c  | 0.979 abc |
| 27 | 12 | 22 cde | 1 c  | 0.6 bc | 0.815 cd |
| 27 | 18 | 44 bcd | 1 c  | 1.2 bc | 0.703 de |
| 27 | 24 | 89 ab  | 69 a | 5.5 a  | 0.592 e |

TABLE 3-continued

Effect of dew period temperature and duration on disease development and biomass of plants inoculated with Phoma sp. isolate A1[a].

| Dew Period Temperature (°C.) | Duration (hr) | Infected leaves (%)[b] | Tissue covered with lesions (%)[c] | Lesions/leaf[d] | Biomass (proportion of control)[e] |
|---|---|---|---|---|---|
| 27 | 30 | 100 a | 76 a | 5.5 a | 0.375 f |

[a]Values in a column followed by the same letter are not significantly different according to the Waller-Duncan K ratio t test ($\alpha = 0.05$).
[b]Data are mean percent infected leaves for leaf two (for each pot of three plants: [total number of infected leaves/total number of leaves] × 100).
[c]Data are mean percent of leaf area of leaf two covered with necrotic tissue as rated with the Barratt-Horsfall scale.
[d]Data are mean numbers of necrotic lesions on leaf two.
[e]Data are means of biomass expressed as proportions of the biomass of uninoculated plants which received the same dew period treatment.

Similar results were obtained when the experiment was repeated with a lower inoculum density except that disease levels and damage were generally lower and no plants were killed. When the experiment was repeated with warmer dew period temperatures (18°, 24°, and 30° C.), 1 of 9 plants was killed in the 18 hr 30° C. treatment, the 24 hr 30° C. treatment, and the 30 hr 24° C. treatment.

EXAMPLE IV

This example illustrates the effect of plant age and Phoma sp. isolate A1 inoculum density on disease severity and biomass of inoculated wild buckwheat plants.

Wild buckwheat seedlings at the 3 to 4-leaf stage (21 days after planting germinated seeds) were inoculated with different inoculum densities (0, $10^5$, $5\times10^5$, $10^6$, $5\times10^6$, $10^7$, $5\times10^7$, or $2.7\times10^8$ spores/m$^2$) and then placed in a dew chamber with an air temperature of 24° C. for 24 hr. Plants were then returned to the growth chamber and incubated for 5 wk. Disease severity was rated on leaf three after 2 wk using the Barratt-Horsfall scale. Disease ratings were converted to midpoint percentages prior to analysis. After 5 wk, mortality was recorded and plants were harvested by cutting the stems at the height of the cotyledons. Plants were placed in paper bags, dried at 60° C. for 7 days, and weighed. There were five pots per treatment with three plants per pot.

For plants at the 3-leaf stage, disease severity increased with increasing inoculum density (Table 4). Percentage of leaves infected increased to 100% at the highest inoculum density tested (Table 4) and percentage of leaf area covered with lesions also increased with increasing inoculum density although the maximum disease severity was only 15% (Table 4). There was a decrease in plant biomass with increasing inoculum density (Table 4) but no mortality occurred at any inoculum density.

TABLE 4

Effect of inoculum density of Phoma sp. isolate A1 on disease development and biomass of inoculated plants[a].

| Inoculum density (log spores/m$^2$) | Infected leaves (%)[b] | Tissue covered with lesions (%)[c] | Lesions/leaf[d] | Biomass (proportion of control)[e] |
|---|---|---|---|---|
| 5 | 13 c | 0 b | 0.0 a | 1.099 a |
| 5.7 | 7 c | 0 b | 0.0 a | 0.859 ab |
| 6 | 27 c | 1 b | 0.0 a | 1.020 ab |
| 6.7 | 60 b | 2 b | 0.0 a | 0.960 ab |
| 7 | 80 ab | 4 b | 0.8 a | 0.963 ab |
| 7.7 | 93 a | 5 b | 1.4 a | 0.758 b |
| 8.4 | 100 a | 15 a | 2.0 a | 0.789 b |

[a]Values in a column followed by the same letter are not significantly different according to the Waller-Duncan K ratio t test ($\alpha = 0.05$).
[b]Data are mean percent infected leaves for leaf three (for each pot of three plants: [total number of infected leaves/total number of leaves] × 100).
[c]Data are mean percent of leaf area of leaf three covered with necrotic tissue as rated with the Barratt-Horsfall scale.
[d]Data are mean numbers of necrotic lesions on leaf three.
[e]Data are means of biomass expressed as proportions of the biomass of uninoculated plants.

Wild buckwheat plants at three different ages (7, 14, and 21 days after planting corresponding to cotyledon, 2-leaf, and 3 to 4-leaf stages) were inoculated with conidia of Phoma sp. isolate A1 in deionized water adjusted to different inoculum densities (0, $10^8$, $10^9$, or $8.9\times10^9$ spores/m$^2$). Inoculated plants were incubated in a dew chamber at 24° C. for 18 hr prior to incubating them in growth chambers or a greenhouse mist frame as above. Disease severity was rated 2 wk after inoculation and plants were rated for mortality and harvested as above after 3 wk. There were three plants per pot and four pots per treatment. The experiment was repeated once using the same inoculum densities and twice using lower inoculum densities ($10^7$, $10^8$, and $10^9$ conidia/m$^2$, and $1.5\times10^6$, $1.5\times10^7$, and $1.5\times10^8$ conidia/m$^2$).

When plants were inoculated at different growth stages and incubated in the growth chamber or greenhouse mist frame, there were interactions between incubation location and inoculum density and/or plant age for percentage of infected leaves. Thus effects of inoculum density, plant age, and their interaction were investigated separately for each location. In the growth chamber, inoculum density had no significant effect on percentages of infected target leaves (i.e. cotyledons for 7-day old plants, leaf 2 for 14-day old plants, and leaf 3 for 21-day old plants) but percentages of infected leaves decreased for 14 and 21-old plants compared to 7 day-old plants (Table 5). In the mist frame, percentages of infected target leaves increased with increasing inoculum density and decreased with increasing plant age (Table 5).

TABLE 5

Effect of inoculum density of Phoma sp. isolate A1 and plant age on disease development on inoculated wild buckwheat plants[a].

| Plant age (days) | Inoculum density (log condida/m$^2$) | Infected leaves (%)[b] in: Growth chamber | Infected leaves (%)[b] in: Mist frame |
|---|---|---|---|
| 7 | 8 | 96 a | 96 a |
| 7 | 9 | 100 a | 96 a |
| 7 | 9.9 | 92 ab | 92 a |
| 14 | 8 | 17 d | 58 ab |
| 14 | 9 | 42 cd | 100 a |
| 14 | 9.9 | 50 cd | 83 a |
| 21 | 8 | 25 cd | 25 b |
| 21 | 9 | 58 bc | 83 a |
| 21 | 9.9 | 25 cd | 67 ab |

[a]Values in a column followed by the same letter are not significantly different according to the Waller-Duncan K ratio t test ($\alpha = 0.05$).
[b]Data are mean percent infected leaves for leaf three (for each pot of three plants: [total number of infected leaves/total number of leaves] × 100).

There was no significant effect of location or interaction between location and other factors on disease severity measured using the Barratt-Horsfall scale and converted to midpoint percentages, mortality, or biomass of plants expressed as a proportion of the uninoculated controls. Thus data were pooled over both locations. Percentage of leaf area covered with lesions increased with increasing inoculum density but it also decreased with increasing plant age (Table 6). The highest level of mortality occurred on plants inoculated when they were 7 days old with the highest inoculum density, but due to the high level of variability there were no significant differences between this treatment and the other two inoculum densities on 7-day old plants (Table 7). No mortality occurred in any other treatment. Applications of Phoma sp. significantly reduced plant biomass expressed as proportions of controls (FIG. 6). There was also a significant effect of plant age on biomass proportion. It would thus appear that older plants are more resistant to infection and/or damage by Phoma sp. since disease severity was less on older plants and biomass proportions of controls were higher on older plants. Only 7-day old plants were killed, however, and if biomass proportion is expressed on a per plant basis only for plants still alive at the conclusion of the experiment, there was a significant effect only of inoculum density and no significant effect of plant age. Thus the biomass proportions of plants of all three ages were affected similarly by Phoma sp. at different inoculum densities. The differences in disease severity detected on plants of different ages might also be due to differences in application rate or variable plant morphology.

TABLE 6

Effect of inoculum density of Phoma sp. and plant age on disease development and plant biomass[a].

| Plant age (days) | Inoculum density (log conodia/$m^2$) | Tissue covered with lesions (%) | Biomass (proportion of control) per pot[c] | Biomass (proportion of control) per plant[c] |
| --- | --- | --- | --- | --- |
| 7 | 8 | 27 b | 0.763 ab | 0.835 a |
| 7 | 9 | 62 a | 0.606 bcd | 0.720 ab |
| 7 | 9.9 | 57 a | 0.486 d | 0.677 ab |
| 14 | 8 | 1 c | 0.779 ab | 0.779 ab |
| 14 | 9 | 5 c | 0.734 abc | 0.734 ab |
| 14 | 9.9 | 3 c | 0.554 cd | 0.554 b |
| 21 | 8 | 1 c | 0.898 a | 0.898 a |
| 21 | 9 | 5 c | 0.766 ab | 0.766 ab |
| 21 | 9.9 | 5 c | 0.745 abc | 0.745 ab |

[a]Values in a column followed by the same letter are not significantly different according to the Waller-Duncan K ratio t test ($\alpha = 0.05$).
[b]Data are mean percent of leaf area of leaf three covered with necrotic tissue as rated with the Barratt-Horsfall scale.
[c]Data are means of biomass expressed as proportions of the biomass of uninoculated plants.

TABLE 7

Mortality (%) of wild buckwheat plants 5 wk after inoculation with different inoculum densities of Phoma sp. isolate A1[a].

| Plant age (days) | Inoculum density (log condida/$m^2$) | | | |
| --- | --- | --- | --- | --- |
| | 0 | 8 | 9 | 9.9 |
| 7 | 0 | 8 | 17 | 29 |
| 14 | 0 | 0 | 0 | 0 |
| 21 | 0 | 0 | 0 | 0 |

[a]Data are mean percent mortality pooled for both locations. Analysis of variance of the three treatments in which mortality occured indicated no significant effect of inoculum density ($\alpha = 0.05$).

When the same experiments were conducted using lower inoculum densities, similar results were obtained except that no mortality occurred even on young plants.

EXAMPLE V

This example illustrates the effect of Phoma sp. applied in combination with chemical herbicides on biomass and mortality of wild buckwheat plants.

Plants at the 2-leaf stage (14 days after planting germinated seeds) were inoculated with four different inoculum densities of Phoma sp. isolate A1 alone and in all combinations with four different chemical herbicide rates. The herbicides MCPA (2-methyl-4-chlorophenoxyacetic acid) and dicamba (3,6-dichloro-o-anisic acid) were tested since both are recommended for wild buckwheat control. Chemical rates were selected by treating wild buckwheat seedlings with the chemical alone in preliminary experiments and selecting a rate which had some effect on biomass but caused no mortality of wild buckwheat. This rate was taken as the highest rate (X) and two lower rates ($\frac{1}{3}$ X and $\frac{2}{3}$ X) plus 0 were used in the experiments. Rates of Phoma sp. varied depending on the availability of inoculum but were between $3 \times 10^6$ and $8 \times 10^8$ spores/$m^2$. Treated plants were incubated in the dew chamber at 24° C. air temperature for 18 hr and were subsequently incubated in a greenhouse mistframe for 3 wk. The mistframe was calibrated to maintain leaf moisture during the night. Natural light was supplemented with 400 W high pressure sodium lamps (14-hr photoperiod, 0600–1800 hr, approximately 50 uEm$^{-2}$s$^{-1}$ supplemental light. Plants were harvested and rated for mortality after 3 wk. There were 3 plants per pot and 4 pots per treatment. Data were analyzed with a factorial analysis of variance and the type of interaction between the two components was evaluated using the method of Drury.

There was a significant synergistic interaction between Phoma sp. and dicamba to increase wild buckwheat mortality (Tables 8,9). Phoma alone caused no mortality of wild buckwheat while dicamba alone caused 17–25% mortality at the two highest rates. In combination, however, they caused 100% mortality of wild buckwheat. Phoma alone had a small effect on plant biomass (Table 10). Results with MCPA were similar (Tables 11-13).

TABLE 8

Effect of Phoma sp. isolate A1 and dicamba on mortality of wild buckwheat plants[a].

| Dicamba rate (kg/ha) | Control (no Phoma) | Phoma rate (log conidia/$m^2$) | | |
| --- | --- | --- | --- | --- |
| | | 7.51 | 7.71 | 8.94 |
| 0.0 | 0 | 0 | 0 | 0 |
| 0.1 | 0 | 0 | 42 | 42 |
| 0.2 | 25 | 50 | 83 | 50 |
| 0.3 | 17 | 42 | 67 | 100 |

[a]Data were analyzed with polynominal regression but only treatment means are presented here ([number of dead plants/total number of plants] × 100).

TABLE 9

Type of interaction between Phoma sp. and dicamba to increase wild buckwheat mortality[a].

| Dicamba rate (kg/ha) | Phoma rate (spores/$m^2$) | | |
| --- | --- | --- | --- |
| | 7.51 | 7.71 | 8.94 |
| 0.1 | S | S | V |
| 0.2 | S | S | V |
| 0.3 | S | S | V |

[a]S = synergistic interaction to increase wild buckwheat mortality; V = Phoma promoted the action of the chemical but not vice versa.

TABLE 10

Effect of Phoma sp. isolate A1 and dicamba on biomass of wild buckwheat plants[a].

| Dicamba rate (kg/ha) | Control (no Phoma) | Phoma rate (log condida/m$^2$) | | |
|---|---|---|---|---|
| | | 7.51 | 7.71 | 8.94 |
| 0.0 | 2.6 | 2.7 | 2.2 | 2.0 |
| 0.1 | 0.7 | 1.1 | 0.5 | 0.5 |
| 0.2 | 0.4 | 0.4 | 0.2 | 0.1 |
| 0.3 | 0.4 | 0.2 | 0.1 | 0.0 |

[a]Data were analyzed with polynominal regression but only treatment means are presented here (g/pot).

TABLE 11

Effect of Phoma sp. isolate A1 and MCPA on mortality of wild buckwheat plants[a].

| MCPA rate (kg/ha) | Control (no Phoma) | Phoma rate (log conidia/m$^2$) | | |
|---|---|---|---|---|
| | | 7.6 | 8.0 | 8.6 |
| 0.0 | 0 | 0 | 0 | 0 |
| 0.1 | 0 | 42 | 33 | 67 |
| 0.2 | 0 | 25 | 25 | 100 |
| 0.3 | 58 | 42 | 83 | 100 |

[a]Data were analyzed with polynominal regression but only treatment means are presented here ([number of dead plants/total number of plants] × 100).

TABLE 12

Type of interaction between Phoma sp. and MCPA to increase wild buckwheat mortality[a].

| MCPA rate (kg/ha) | Phoma rate (spores/m$^2$) | | |
|---|---|---|---|
| | 7.6 | 8.0 | 8.6 |
| 0.4 | C* | S | S |
| 0.8 | A* | A | A |
| 1.2 | S | S | C* |

[a]S = synergistic interaction to increase wild buckwheat mortality, A* = antagonistic interaction to increase wild buckwheat mortality, C* = MCPA promoted the action of Phoma but not vice versa and the interaction resulted in a decrease in mortality. A = antagonistic interaction to decrease wild buckwheat mortality.

TABLE 13

Effect of Phoma sp. isolate A1 and MCPA on biomass of wild buckwheat plants[a].

| MCPA rate (kg/ha) | Control (no Phoma) | Phoma rate (log condida/m$^2$) | | |
|---|---|---|---|---|
| | | 7.6 | 8.0 | 8.6 |
| 0.0 | 1.5 | 1.7 | 1.2 | 1.3 |
| 0.4 | 1.0 | 0.3 | 0.4 | 0.1 |
| 0.8 | 0.6 | 0.5 | 0.3 | 0.0 |
| 1.2 | 0.2 | 0.4 | 0.0 | 0.0 |

[a]Data were analyzed with polynominal regression but only treatment means are presented here (g/pot).

What is claimed is:

1. A method for controlling growth of *Polygonum convolvulus* weeds in agricultural crops which method comprises applying to said weeds or to the locus of said weeds an effective amount of the fungus Phoma sp. having the culture deposit No. ATCC 20982, in combination with a chemical herbicide selected from the group consisting of dicamba and MCPA, to effect and produce typical lesions in said weeds so as to inhibit the growth of or kill said weeds.

2. The method of claim 1, wherein the chemical herbicide is dicamba.

3. The method of claim 1, wherein the chemical herbicide is MCPA.

4. A composition for controlling growth of *Polygonum convolvulus* weeds in agricultural crops, comprising an effective amount of the fungus Phoma sp. having the culture deposit No. ATCC 20982, and a chemical herbicide selected from the group consisting of dicamba and MCPA, in association with an agricultural carrier.

5. A composition according to claim 4, wherein the concentration of the fungus is from about $10^3$ to $10^7$ spores/ml of carrier.

6. A composition according to claim 4, wherein the chemical herbicide is dicamba.

7. A composition according to claim 4, wherein the chemical herbicide is MCPA.

* * * * *